United States Patent
Hawthorne et al.

(10) Patent No.: US 7,311,665 B2
(45) Date of Patent: Dec. 25, 2007

(54) BIO-INFORMATION SENSOR MONITORING SYSTEM AND METHOD

(75) Inventors: Jeffrey Scott Hawthorne, Bennett, CO (US); Michael Leonard Iiams, Littleton, CO (US); Glenn Charles Tubb, Englewood, CO (US); Richard A. Stoll, Morrison, CO (US); Gary Alan Shoffner, Westminster, CO (US)

(73) Assignee: Alcohol Monitoring Systems, Inc., Littleton, CO (US)

( * ) Notice: Subject to any disclaimer, the term of this patent is extended or adjusted under 35 U.S.C. 154(b) by 0 days.

(21) Appl. No.: 10/441,960

(22) Filed: May 19, 2003

(65) Prior Publication Data

US 2004/0236189 A1    Nov. 25, 2004

(51) Int. Cl.
 *A61B 5/00* (2006.01)
(52) U.S. Cl. .................. 600/300; 600/301; 128/920
(58) Field of Classification Search ........ 600/300–301; 128/903, 904, 920–925; 705/2–4; 340/573.1
See application file for complete search history.

(56) References Cited

U.S. PATENT DOCUMENTS

| | | | |
|---|---|---|---|
| 4,173,971 A | 11/1979 | Karez | 600/515 |
| 4,749,553 A | 6/1988 | Lopez et al. | 422/84 |
| 4,868,545 A | 9/1989 | Jones | 340/573.1 |
| 4,916,435 A | 4/1990 | Fuller | 340/573.4 |
| 4,999,613 A | 3/1991 | Williamson et al. | 340/573.4 |
| 5,033,293 A | 7/1991 | Honma et al. | 73/118.1 |
| 5,220,919 A | 6/1993 | Phillips et al. | 600/345 |
| 5,303,575 A | 4/1994 | Brown et al. | 73/23.3 |
| 5,724,025 A * | 3/1998 | Tavori | 600/300 |
| 6,024,699 A * | 2/2000 | Surwit et al. | 600/300 |
| 6,443,890 B1 * | 9/2002 | Schulze et al. | 600/300 |
| 6,524,239 B1 * | 2/2003 | Reed et al. | 600/300 |
| 6,726,636 B2 | 4/2004 | Der Ghazarian et al. | 600/532 |
| 7,051,120 B2 | 5/2006 | Greene et al. | 709/250 |
| 2002/0156650 A1 | 10/2002 | Klein et al. | 705/2 |
| 2003/0126593 A1 | 7/2003 | Mault | 725/10 |

FOREIGN PATENT DOCUMENTS

WO    WO 2002/12883    2/2002    .................. 33/497

OTHER PUBLICATIONS

Towa, Rene T., Office Action Summary, Jul. 11, 2006.
Towa, Rene T., Office Action Summary, Nov. 29, 2006.
Towa, Rene T., Office Action Summary, May 10, 2007.

* cited by examiner

*Primary Examiner*—Max F. Hindenburg
*Assistant Examiner*—Michael C Astorino
(74) *Attorney, Agent, or Firm*—Merchant & Gould PC; Stanley J. Gradisar (57) ABSTRACT

A bio-information monitoring system passively monitors a patient with a remote portable bio-information unit that takes various bio-information measurements at selected time intervals as well as at random times without patient intervention. The measurements are converted to digital signals which are transmitted from the bio-information unit to a modem when the bio-information unit is in proximity to the modem. The signals are stored in the modem and uploaded to a central monitoring network. Automatic alerts may be sent from the central monitoring network to a treatment provider. The treatment provider may also access the information through secured dedicated websites via the Internet.

47 Claims, 5 Drawing Sheets

BIO-INFORMATION SENSOR MONITORING SYSTEM AND METHOD

CROSS REFERENCE TO RELATED APPLICATION

This application is related to a co-pending patent application Ser. No. 10/441,940 by Hawthorne et al. titled "METHOD AND APPARATUS FOR REMOTE BLOOD ALCOHOL MONITORING" and filed on the same day herewith, which is owned by the same assignee of this invention.

FIELD OF THE INVENTION

This invention relates to medical monitoring systems, and more particularly, relates to an improved passive method and system for monitoring bio-information of a subject.

BACKGROUND OF THE INVENTION

In-home monitoring for the purpose of health management of chronic disease patients typically requires the patients to attach monitors of various kinds to their bodies, actuate the monitors to take various bio-information readings, and then hook up the monitor to a communication device, and then send the readings taken to a monitoring station or health care provider. Various types of monitors may be used to gather bio-information data regarding the patient. Such monitors may take the patient's blood pressure, temperature, pulse, $SpO_2$, CO, ICG, ECG, respiration, blood glucose, and the like. Such information can provide valuable feedback on the health status of the patient to the health care provider. Current technology allows for patients to take regular measurements at home that get collected and transferred, typically via a standard telephone line, to a data collection system, or directly to a health care provider. This methodology is a significant improvement over techniques that require patients to keep written logs of measurements taken themselves. Such written logs are subject to errors or missing data, and are usually only reviewed by a healthcare provider during routine checkups. In addition, some patients do not want to cooperate and take the readings that are needed, posing an additional problem to the healthcare provider.

There is a need for a remote bio-information monitoring system which can be passively used by the patient that can take the various measurements at selected time intervals as well as at random times without patient intervention. There is also a need to be able to download the bio-information measurements to a monitoring station or healthcare provider without requiring any actions on the part of the patient being monitored, eliminating the need for the patient to personally record the measurements, or connect the monitoring device to a telephone line to download and transmit the data. The present invention meets these and other needs in the art.

DETAILED DESCRIPTION OF THE INVENTION

Figure 1:
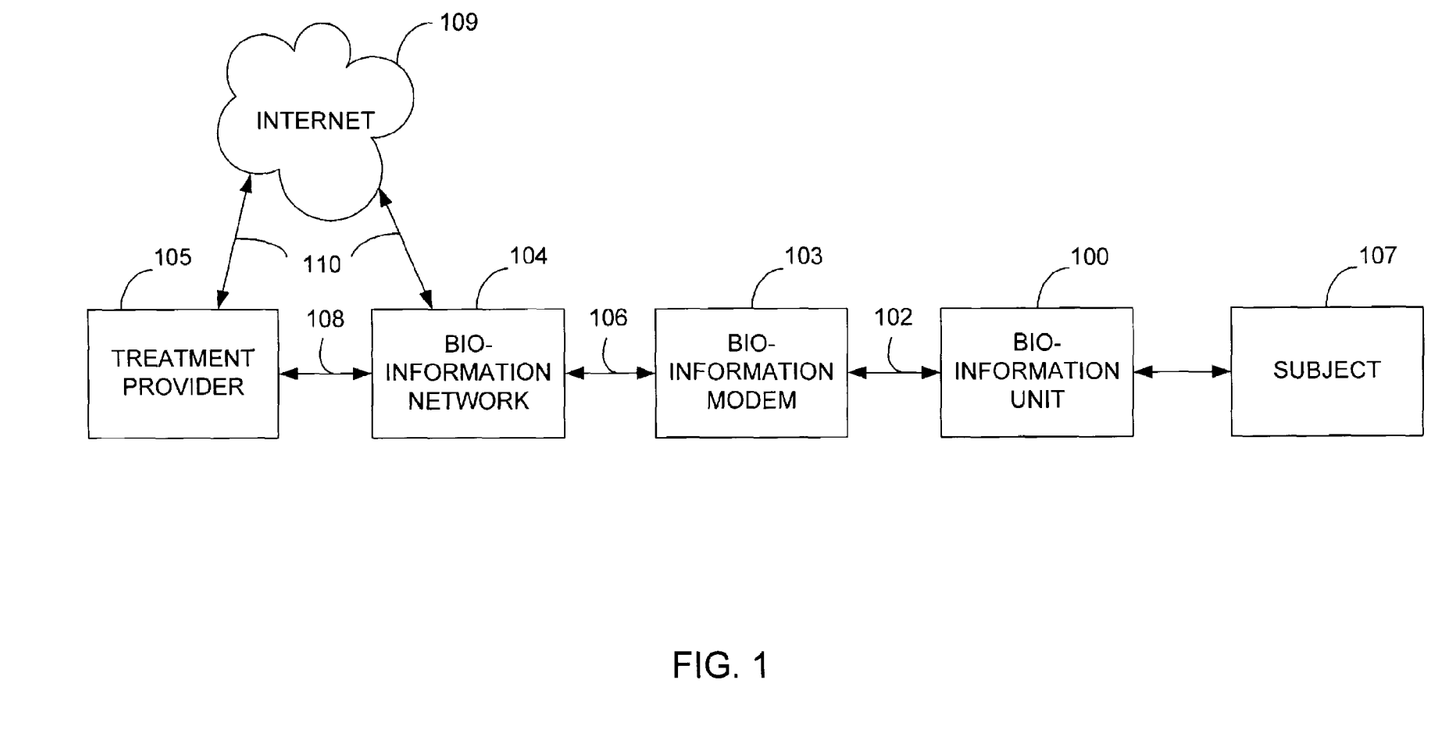
FIG. 1 shows a block diagram of the bio-information sensor monitoring system of the present invention.

FIG. 1 shows a block diagram of the bio-information sensor monitoring system of the present invention. The system and method is designed to collect, store and forward the information measured, sensed, or otherwise captured by various bio-sensors to a central web-hosted database, where treatment providers can gain access to the data collected by the bio-sensors. The system and method provides a portable means for the bio-information to be collected. The system and method can be used to remotely monitor any biological data including, but not limited to, blood oxygen, blood carbon dioxide, insulin levels, heart rate, temperature, respiration, and any other biological data based on the specific bio-sensor(s) being used in the bio-information unit. The system allows for the one or more portable bio-sensors to be worn, attached, or otherwise utilized by a subject for an extended period of time in an untethered fashion. The data collected by the bio-information unit is wirelessly forwarded to a bio-information modem that in turn forwards the collected data to a central web-hosted database where treatment providers can easily access the data collected.

Referring now to FIG. 1, a portable Bio-Information Unit 100 is worn, attached, or otherwise utilized by Subject 107 being monitored. Bio-Information Unit 100 will take readings from the one or more bio-sensors associated with it at predetermined or random intervals 24 hours a day, 7 days a week, 365 days a year. Periodically Subject 107 with Bio-Information Unit 100 comes within range of Bio-Information Modem 103. When Bio-Information Unit 100 is within range of Bio-Information Modem 103, and the timer indicates that it is time to communicate with Bio-Information Modem 103, the Bio-Information Unit 100 will transfer all the data taken from the readings collected and stored, along with any error indicators and any other diagnostic data stored to Bio-Information Modem 103. Bio-Information Modem 103 then stores all of this information for transmission to Bio-Information Network 104. After receiving all of the information from Bio-Information Unit 100, Bio-Information Modem 103 will check the stored data for any readings or errors. Either of these, or a trigger from a predetermined time interval, will cause Bio-Information Modem 103 to communicate with Bio-Information Network 104, typically through the telephone system via Communication Link 106. Once Communication Link 106 is established between Bio-Information Modem 103 and Bio-Information Network 104, Bio-Information Modem 103 will transfer all of the readings, errors, and any other diagnostic data it has stored to Bio-Information Network 104. Bio-Information Network 104 then analyzes the data received and separates and groups the data into a number of separate categories for reporting to Treatment Provider 105. The data can then be accessed by the monitoring personnel of Treatment Provider 105 through the use of secured dedicated websites through the Internet 109 and Internet Connections 110 to Bio-Information Network 104.

The communication link between Bio-Information Unit 100 and Bio-Information Modem 103 is established through a bi-directional radio frequency ("RF") Communication Link 102. RF Communication Link 102 provides a means for Bio-Information Modem 103 to set up the appropriate reading schedules and communication schedules for Bio-Information Unit 100. The reading schedules and communications schedules are set up by Treatment Provider 105 through Bio-Information Network 104. RF Communication Link 102 also provides a means for Bio-Information Modem 103 to monitor the status of the operating program of Bio-Information Unit 100, and to update this program when needed. RF Communication Link 102 also provides a means for Bio-Information Unit 100 to upload its stored readings, errors, and diagnostic data to Bio-Information Modem 103.

All of the communication between Bio-Information Modem 103 and Bio-Information Unit 100 is sent over RF Communication Link 102 in a proprietary RF encoded format. This format is similar to a standardized serial TCP/IP format with RF encoding. To ensure that the data being sent over RF Communication Link 102 is valid, each packet sent from Bio-Information Unit 100 to Bio-Information Modem 103 must be validated by Bio-Information Modem 103 before being erased from memory by Bio-Information Unit 100. The validation process insures that no data will be lost during the transfer should the transfer be interrupted by some type of interference, or if Subject 107 moves out of range of Bio-Information Modem 103 during the transfer.

Once Bio-Information Modem 103 has received all of the data from Bio-Information Unit 100, it stores the data and then checks to see if there is any information in the data received that needs to be transmitted immediately. If not, Bio-Information Modem 103 will transmit the data on scheduled times only. Bio-Information Modem 103 is equipped with a Real Time and date Clock ("RTC") used to monitor the calendar date and the current time. This provides a means for Bio-Information Modem 103 to check on programmable schedules to see when the data should be transmitted to Bio-Information Network 104.

Once Bio-Information Modem 103 decides that it is time to transmit data to Bio-Information Network 104, it will turn off RF Communication Link 102 if it is currently on. Bio-Information Modem 103 will then turn on Modem Chip Set 326 (see FIG. 3) which is connected via a telephone line to Communication Link 106. Bio-Information Modem 103 will then check to see if a dial tone is available. If no dial tone is available, then Bio-Information Modem 103 will log an alarm indicating no dial tone, and wait a predetermined period of time, such as one minute, before attempting to dial again. Once a dial tone is established, Bio-Information Modem 103 will dial the number to connect to Bio-Information Network 104. When Bio-Information Network 104 answers the call, Modem Chip Set 326 will establish a connection via Communication Link 106. Bio-Information Network 104 will then establish communication with Bio-Information Modem 103.

Bio-Information Network 104 will first execute a series of inquiries used to validate Bio-Information Modem 103. Once Bio-Information Modem 103 is validated, Bio-Information Network 104 will then retrieve all of the information stored in Bio-Information Modem 103. Each data packet sent from Bio-Information Modem 103 must be validated by Bio-Information Network 104 before it is erased from memory by Bio-Information Modem 103. This validation process makes sure that no data will be lost during the transfer from Bio-Information Modem 103 to Bio-Information Network 104 if Communication Link 106 should be interrupted for whatever reason.

After all of the information has been received, Bio-Information Network 104 will check the status of the program stored in Bio-Information Modem 103, as well as the status of the program stored in Bio-Information Unit 100. If either program is out of date, then Bio-Information Network 104 will send an updated program to Bio-Information Modem 103, which will update the program stored in Bio-Information Unit 100 upon the next communication session with Bio-Information Unit 100. Bio-Information Network 104 will then update all schedule information for Bio-Information Modem 103 and Bio-Information Unit 100.

Bio-Information Network 104 will then sort all of the data into the appropriate categories and decide if any immediate notification action needs to be taken. If notification is needed, then Bio-Information Network 104 will perform the desired notification operations, such as sending out a page, an e-mail, a phone mail message, a fax, etc. to monitoring personnel at Treatment Provider 105 via Communication Link 108.

Treatment Provider 105 can access the data which triggered the alert by accessing the Internet 109 through Internet Connections 110 and logging into the appropriate secure web site. From the secure web site, Treatment Provider 105 can then review the alert, print reports of the desired data, as well as change any schedules or make any adjustments to the equipment operation, or contact Subject 102 if necessary.

Figure 2:
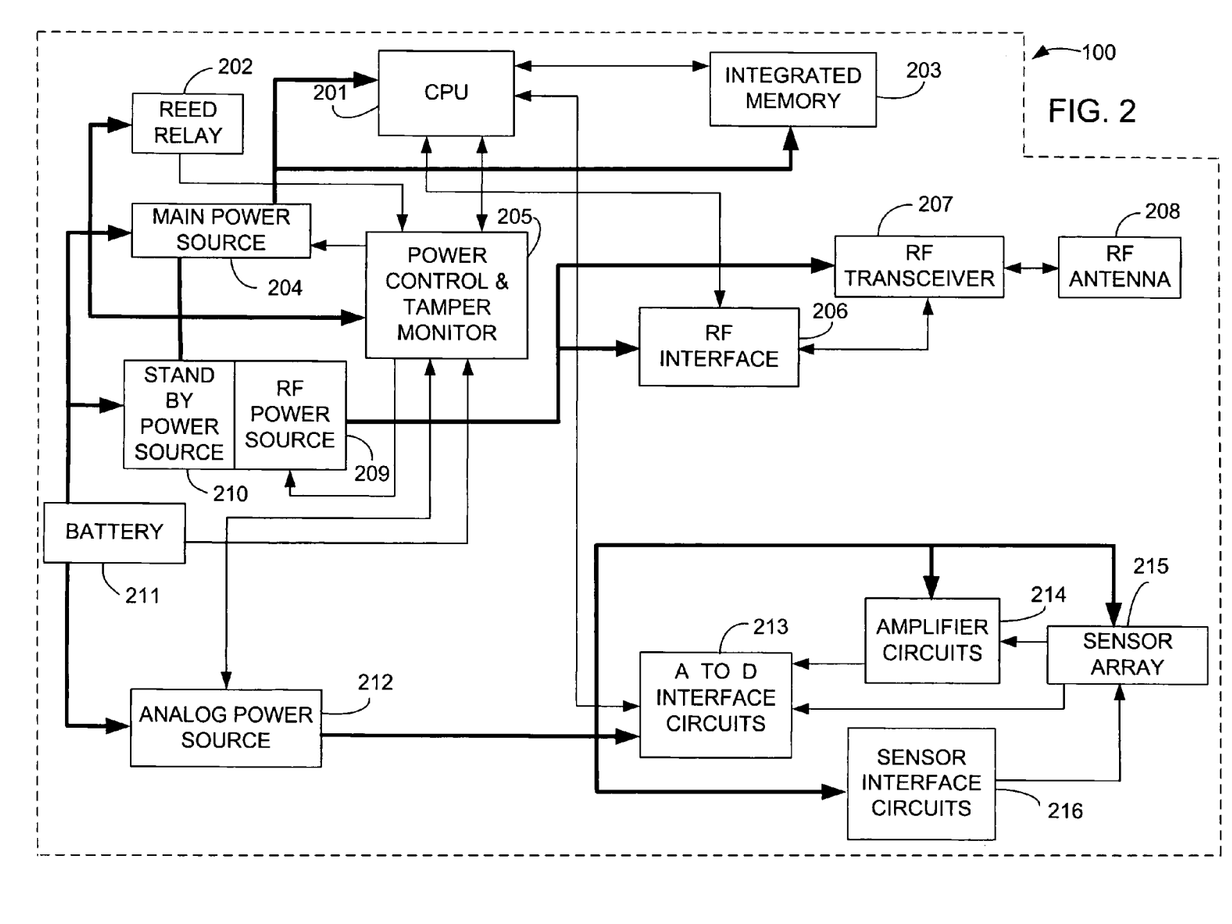
FIG. 2 shows a block diagram of the Bio-Information Unit 100 of FIG. 1.

FIG. 2 shows a block diagram of the Bio-Information Unit 100 of FIG. 1 where thicker arrows represent power circuits, and thinner arrows represent signal circuits. Referring now to FIG. 2, Bio-Information Unit 100 contains a microcontroller that functions as a Power Controller 205. Power Controller 205 controls all of the power in Bio-Information Unit 100. When the Battery 211 is inserted into Bio-Information Unit 100, Power Controller 205 is activated by Stand By Power Source 210, which causes Bio-Information Unit 100 to operate at a low voltage level. Once Power Controller 205 is initialized and running, it will turn on the main power to Bio-Information Unit 100 by activating Main Power Source 204. Power Controller 205 will then operate at the main power level with the rest of the circuits. Another function of Power Controller 205 is to monitor the output power level of Battery 211 that powers Bio-Information Unit 100. This is accomplished by running the raw battery voltage through a resistive voltage divider and then connecting it directly to Power Controller 205. Power Controller 205 also controls the power to the analog circuits and an optional analog board, (which may be present in some types of Bio-Information Units 100) through Analog Power Source 212. The optional analog board provides a means of adapting Bio-Information Unit 100 to a large assortment of bio-medical equipment. Analog Power Source 212 in turn provides the power to the Analog to Digital ("A to D") Interface Chip 213 and the Sensor Interface Circuits 216, so that the circuits are not powered up the entire time that Bio-Information Unit 100 is turned on.

Another function of Power Controller 205 is to provide a real time clock. The time and date are downloaded to CPU 201 from Bio-Information Modem 103 and are then communicated to Power Controller 205. This Process synchronizes the Bio-Information Unit 100 with the Bio-Information Modem 103. This process will occur every time the two devices communicate with each other. The Bio-Information Modem 103 also synchronizes it's time and date with the Bio-Information Network 104 each time that they communicate. Power Controller 205 will then keep track of the time and date and automatically turn on Main Power Source 204 at scheduled times, which can be programmed by CPU 201.

Power Controller 205 monitors all of the inputs that can cause Bio-Information Unit 100 to wake up due to some kind of stimulant condition existing. One condition is if a magnet is passed near Reed Relay 202. Passing a magnet near Reed Relay 202 is a method that may be employed to wake up Bio-Information Unit 100 in order to take a reading at an unscheduled time. Any such activation of Bio-Information Unit 100 is processed as an alert. Monitoring personnel can note in the records that the alert event recorded was a result of Subject 107 actions, thereby providing a means of verifying that Subject 107 took a manual reading at the appropriate time.

Passing a magnet near Reed Relay 202 will cause it to open and close creating a pulsing effect at the power controllers monitoring input. When Power Controller 205 detects this pulsing input it will immediately turn on Main Power Source 204 and activate Bio-Information Unit 100.

Bio-Information Unit 100 also contains CPU 201 which is a stand alone processor which typically has no internal memory component. In another embodiment of the invention, CPU 201 and Integrated Memory 203 may be combined together in the same chip. CPU 201 retrieves all of its instructions and data from Integrated Memory 203. Integrated Memory 203 is divided internally into several different memory segments. There is a small segment of the memory dedicated to the boot strap program. The boot strap program is used to initialize Bio-Information Unit 100 when power is first applied. The boot strap program is a very basic program that will initialize CPU 201 and then check the validity of the main operating program that is stored in a larger section of Integrated Memory 203. The boot strap program also has the capability of establishing communications through RF Communication Link 102 if the main program is not valid.

RF Communication Link 102 is established through the use of a serial to RF Transceiver 207 and RF Antenna 208. CPU 201 will command Power Controller 205 to turn on RF Power Source 209. Power Controller 205 will then activate RF Power Source 209 and supply all the RF components with low voltage. CPU 201 is connected to RF Transceiver 207 through RF Interface 206 which allows the serial signal from CPU 201 to be converted to the proper voltage for the RF transceiver circuits. By establishing RF Communication Link 102 the main program can then be downloaded into Bio-Information Unit 100 by Bio-Information Modem 103 if required. Once the boot strap program has verified that the main program is valid, it will then switch operation to the main program segment in Integrated Memory 203. If the main operating program was verified, then Bio-Information Unit 100 will switch operation to the main program segment in Integrated Memory 203 instead of establishing RF Communication Link 102.

A to D Interface Chip 213 is a programmable A to D converter in that it allows for amplifier gain to be applied to the signals that are being monitored through the use of internal Amplifier Circuits 214 and software stored in Integrated Memory 203, instead of using external hardware to amplify the signals. CPU 201 can then use software stored in Integrated Memory 203 to change the gain of all the A to D channels at any time. A to D Interface Chip 213 is used to convert data captured by Sensor Array 215. Sensor Array 215 may have one or more sensors designed to capture one or more types of bio-information as discussed above. The signals from Sensor Array 215 are input to A to D Interface Chip 213 in analog format and are then converted to a digital signal and communicated through a serial link to CPU 201.

After Bio-Information Unit 100 has been activated by Power Controller 205, and it has confirmed all of the memory functions are good, it will read Sensor Array 215 and record all of the resulting data from each type of sensor that is being monitored at the time. After Bio-Information Unit 100 has completed reading Sensor Array 215, it will then activate the RF circuits and wait to see if a RF signal is received from Bio-Information Modem 103. If a signal is received from Bio-Information Modem 103, Bio-Information Unit 100 will then retrieve all of the information stored in Integrated Memory 203 and transmit it to Bio-Information Modem 103. If no signal is received then Bio-Information Unit 100 will turn off until the next scheduled wake up time.

Figure 3:
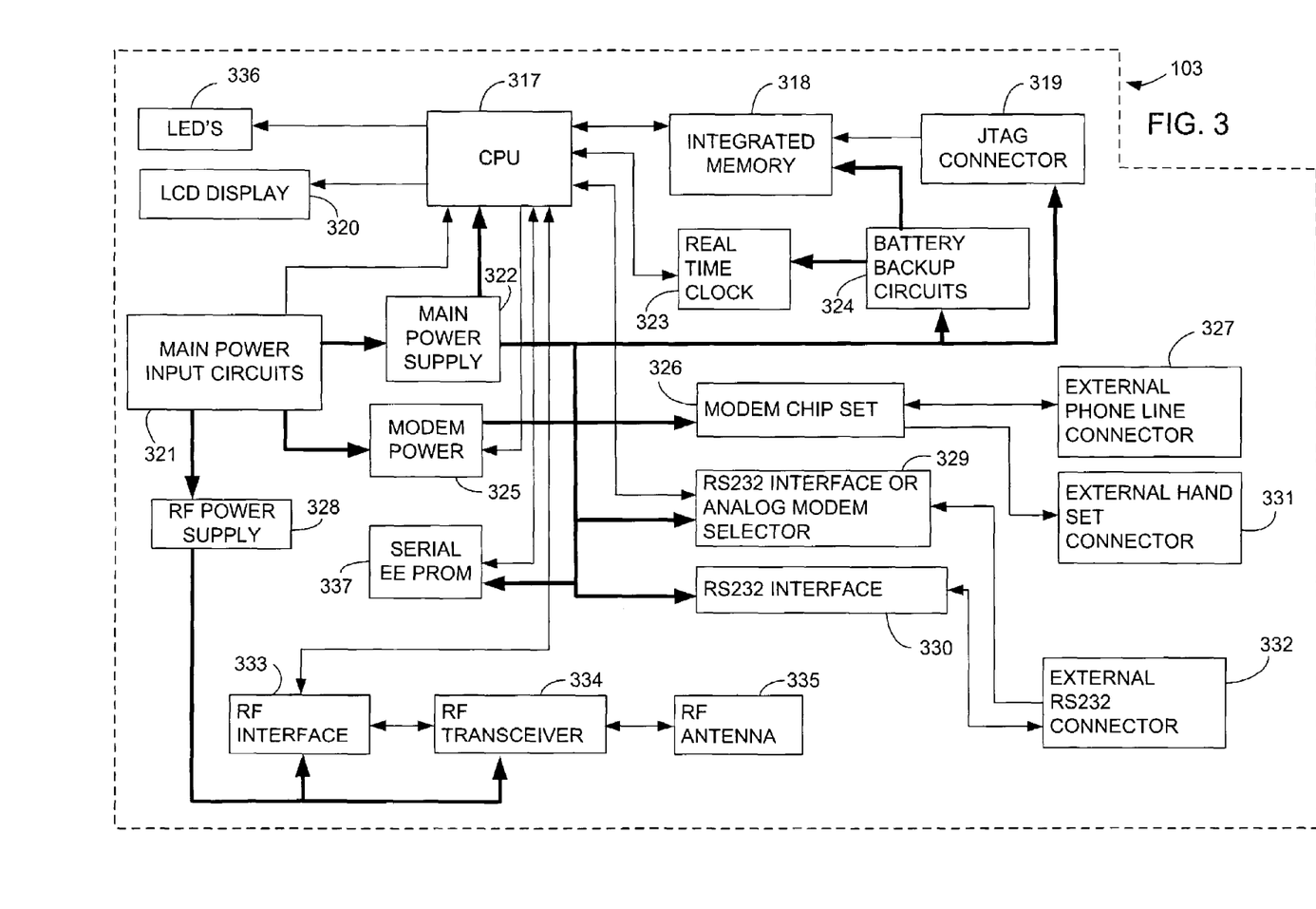
FIG. 3 shows a block diagram of an embodiment of Bio-Information Modem 103.
Figure 4A:
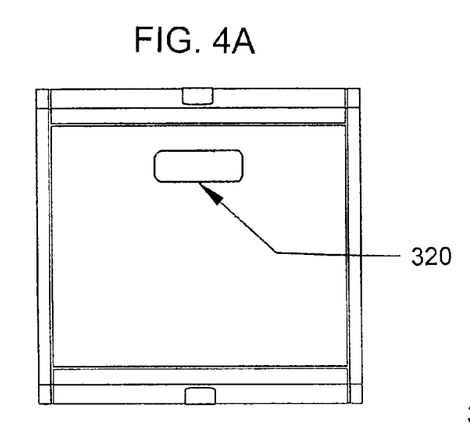
FIGS. 4A, 4B, 4C, and 4D show a top view and three elevation views of the modem in an embodiment of the present invention.
Figure 4B:
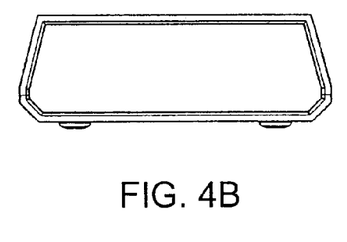
Figure 4C:
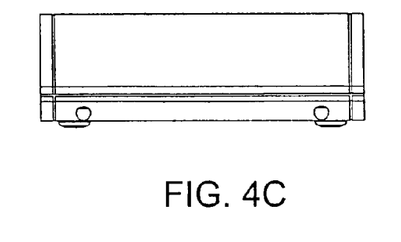
Figure 4D:
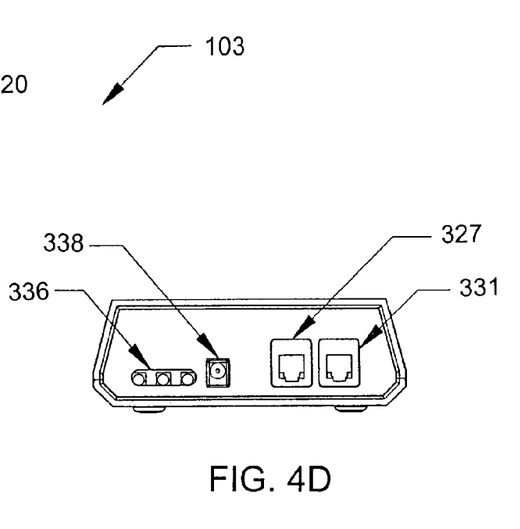

FIG. 3 shows a block diagram of an embodiment of Bio-Information Modem 103 where thicker arrows represent power circuits, and thinner arrows represent signal circuits. FIGS. 4A, 4B, 4C, and 4D show a top and three elevation views of an embodiment of Modem 104. Referring now to FIG. 3 and FIGS. 4A, 4B, 4C, and 4D, Bio-Information Modem 103 is powered by an external dc power supply (not shown in FIG. 3 or FIGS. 4A, 4B, 4C, and 4D). The dc power supply can be configured to plug into either a 115V AC supply or an international type power outlet. The dc power supply is plugged into an external power source and then plugged into the back of Bio-Information Modem 103 at a Main Power Input 338. Main Power Input 338 is connected to Main Power Input Circuits 321. Main Power Input Circuits 321 filter the power and make sure that the polarity of the power is correct and then distributes the power to Main Power Supply 322, Modem Power Supply 325, and RF Power Supply 328. Main Power Input Circuits 321 also monitor the power for AC power failures. This is accomplished by running the DC power input through a resistive divider and then into CPU 317.

Main Power Supply 322 supplies the power to CPU 317, RS232 Interface or Analog Modem Selector 329, RS232 Interface 330, Serial EE Prom 337, Battery Backup Circuits 324 and JTAG Connector 319. Battery Backup Circuits 324 supply the power to Integrated Memory 318 and Real Time Clock 323. The main power is applied as soon as Bio-Information Modem 103 is plugged in. The fact that Bio-Information Modem 103 is on is reflected by at least one LED that is illuminated in LED's 336. LCD Display 320 is also used to display any special instructions or request of Subject 107 by the monitoring personnel. Test results and critical sensor information can also be displayed on LCD Display 320. LCD Display 320 will also display any schedule information that Subject 107 may need to be aware of.

Integrated Memory 318 is divided internally into several different memory segments. There is a small segment of the memory dedicated to the boot strap program. The boot strap program is used to initialize Bio-Information Modem 103 when power is first applied. The boot strap is a very basic program that will initialize CPU 317 and then check the validity of the main operating program that is stored in a larger section of Integrated Memory 318. There is also an additional RAM component that supplies extra data storage capabilities. Serial EE Prom 337 is used to store all of the critical information for Bio-Information Modem 103 such as the serial number, device identification information and the phone numbers that should be called to connect to Bio-Information Network 104. Bio-Information Modem 103 will retrieve and validate all of the critical information and will then validate the main operational program. If the main operational program is valid, Bio-Information Modem 103 will switch operation from the bootstrap program to the main operational program. Once the switch is made Bio-Information Modem 103 will contact Bio-Information Network 104 and report the latest power fail. If the main operational program is not valid than Bio-Information Modem 103 will try to contact Bio-Information Network 104 and get the main operational program downloaded to itself. The JTAG Connector 319 also provides a means of programming both the modem boot strap program and the main operational program into Integrated Memory 318.

To connect to Bio-Information Network 104, Bio-Information Modem 103 will check the input from the RS232 Interface or Analog Modem Selector 329 and see if there is a serial cable attached to Bio-Information Modem 103 at External RS232 Connector 332, which is accessible by opening up the cover of Bio-Information Modem 103. If there is, then Bio-Information Modem 103 will go into slave mode waiting for serial communications to come in through RS232 Interface 330. This mode provides a means of manually issuing commands and loading programs and or data to Bio-Information Modem 103. If there is no serial cable attached to Bio-Information Modem 103, then CPU 317 will turn on Modem Power Supply 325. After allowing Modem Chip Set 326 to power up and stabilize, CPU 317 will check for a dial tone. If no dial tone is identified, then CPU 317 will hang up and generate an alarm to indicate that the telephone line is not connected at External Phone Line Connector 327. Bio-Information Modem 103 will then try again after a predefined delay period. External Hand Set Connector 331 receives the telephone wire that comes from the telephone hand set.

Once a dial tone has been established, CPU 317 will dial the telephone number for Bio-Information Network 104. CPU 317 will then monitor Modem Chip Set 326 for an indication that a connection has been established with Bio-Information Network 104. If CPU 317 determines that the telephone line is busy, or that there is no answer, then CPU 317 will hang up and log an alarm indicating that a connection could not be established. Bio-Information Modem 103 will then wait a predefined delay period and try to make the connection again. Once the connection is established, Bio-Information Network 104 becomes the master and Bio-Information Modem 103 becomes the slave. Bio-Information Network 104 will then extract all of the pertinent information that it needs to validate Bio-Information Modem 103 and to update its status. It will then update Real Time Clock 323 so that Bio-Information Modem 103 is set to the proper time for the time zone where Bio-Information Modem 103 is currently located. Bio-Information Network 104 will then upload all data that has been stored in Bio-Information Modem 103 since the last upload. Bio-Information Network 104 then has the ability to download any number of specific monitoring instructions that need to be sent to Bio-Information Unit 100, along with all of the schedule information for Bio-Information Modem 103 and Bio-Information Unit 100. Bio-Information Network 104 will then tell Bio-Information Modem 103 to hang up and start operations.

CPU 317 will hang up and turn off the power to Modem Chip Set 326. CPU 317 will then activate the RF circuits and try to establish RF Communication Link 102. RF Communication Link 102 is established through the use of a serial to RF Transceiver 334 and the RF antenna 335. CPU 317 is connected to RF transceiver 334 through RF Interface 333 which allows the serial signal from CPU 317 to be converted to the proper voltage for the RF transceiver circuits. CPU 317 will start sending a standard message out over the RF Communication Link 102. This message is addressed to Bio-Information Unit 100, so if Bio-Information Unit 100 is within range of Bio-Information Modem 103 and Bio-Information Unit 100 is active, then Bio-Information Unit 100 will answer the message with a status message indicating that Bio-Information Unit 100 is active and operating. Bio-Information Modem 103 will then become the master and Bio-Information Unit 100 will become the slave. Bio-Information Modem 103 will extract all of the status information from Bio-Information Unit 100 and will validate the operating program and any pertinent operating data needed by Bio-Information Unit 100. Bio-Information Modem 103 will then update the real time clock in Bio-Information Unit 100 SO that Bio-Information Unit 100 and Bio-Information Modem 103 are on the same time. Bio-Information Modem 103 will then extract any sensor reading information as well as any error information from Bio-Information Unit 100. Bio-Information Modem 103 will then turn off the RF signal. When the RF signal is turned off, Bio-Information Unit 100 will turn itself off and return to normal monitoring mode.

CPU 317 will then scan through the data just received and determine if any of the data needs to be sent immediately to Bio-Information Network 104. If not, then CPU 317 will wait a predefined delay period and then start the polling sequence again. If there is data that needs to be transmitted to Bio-Information Network 104 immediately, or if the time clock indicates that it is a scheduled time to call Bio-Information Network 104, then Bio-Information Modem 103 will go through the connection process and connect to Bio-Information Network 104.

Figure 5:
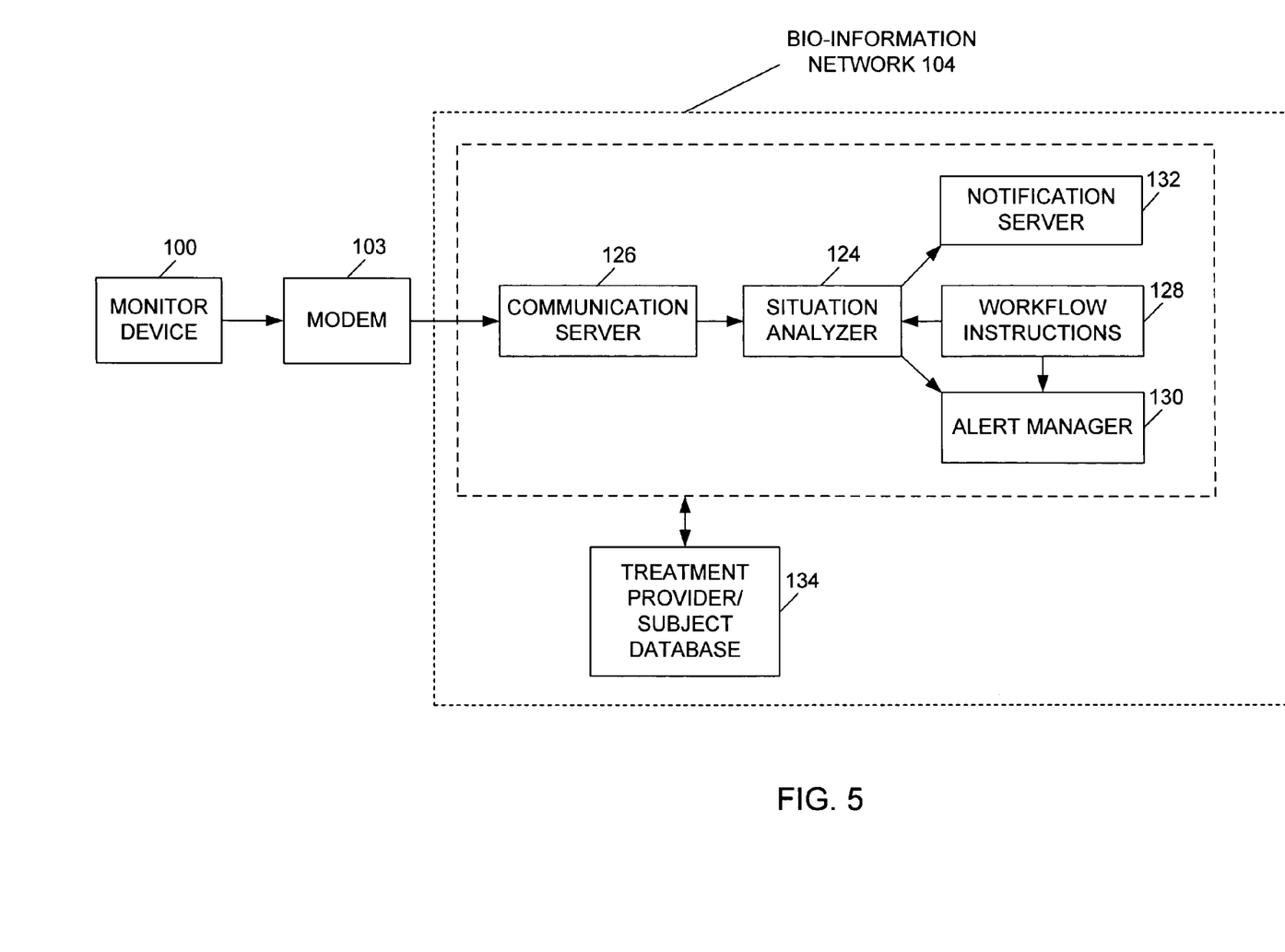
FIG. 5 shows a block diagram of the monitor network in an embodiment of the present invention.

FIG. 5 shows a more detailed block diagram of Bio-Information Network 104. Alert/sensor information is constantly being generated and monitored by the bio-information system components of the present invention. The following description will describe how and why the information is generated and how the information is handled and processed once it is generated.

Once Bio-Information Unit 100 has been adjusted properly for utilization by Subject 107, the battery pack is inserted into Bio-Information Unit 100. When the battery makes electrical contact upon being inserted into Bio-Information Unit 100, an alert is generated indicating that power has been applied to Bio-Information Unit 100. Normal occurrences of these alerts are generated each time Bio-Information Unit 100 is attached to Subject 107 or each time that the battery is changed. The power up alerts provide a means for the monitoring personnel to verify that the equipment is on Subject 107 at the appropriate times. If Subject 107 does not have the equipment on at the appropriate time the monitoring personnel can respond appropriately in case there is a problem with Subject 107. Once Bio-Information Unit 100 is operational Subject 107 simply needs to wear or attach the sensor array required and go about their normal activities. The bio-information data will be collected continuously, and transmitted automatically to the Bio-Information Modem 103.

The alert described previously will cause the Bio-Information Unit 100 to attempt to communicate with the Bio-Information Modem 103 as soon as possible, overriding the normal scheduled communications programmed in the Bio-Information Modem 103 and Bio-Information Unit 100. The bio-information system uses the scheduled communications times to ensure that all equipment is operational under normal conditions. During normal operation there should be no reason for the equipment to override the schedules, and it will only communicate when scheduled. If no schedules were used, there would be no communication and no validation that readings were being taken and stored by Bio-Information Unit 100. If Bio-Information Unit 100 does not communicate at a scheduled communications time, Bio-Information Modem 103 will generate an alert that Bio-Information Unit 100 failed to communicate on schedule, along with the present time and date. This alert will be labeled as a Communications Alert by Situation Analyzer

124. If Bio-Information Unit 100 does not communicate with Bio-Information Modem 103 for a period of 24 hours, Bio-Information Modem 103 will generate a No Communications alert, along with the present time and date. This will also be labeled as a Communications Alert by Situation Analyzer 124. Thus, the normal flow of communications between Bio-Information Unit 100 and Bio-Information Modem 103 must exist or there will be alerts generated to inform the treatment providers that something is wrong with the system.

Bio-Information Modem 103 communicates with Bio-Information Network 104 through Communication Server 126. The normal communication between these two devices is controlled by schedules programmed into the particular Bio-Information Modem 103 utilized with the particular Bio-Information Unit 100. Bio-Information network 104 also monitors these schedules. If Bio-Information Modem 103 fails to communicate when scheduled, Bio-Information Network 104 will generate a Communications Alert indicating that Bio-Information Modem 103 failed to communicate when scheduled. Thus, if the normal communications cycle between Bio-Information Modem 103 and Communication Server 126 is broken, then alerts will be generated to inform the supervising personnel that something is wrong with the system. This type of system architecture provides the means for equipment at each level of the communications chain to generate alarms. This guarantees that if a piece of equipment anywhere in the chain of communication fails, there will be an alarm to report it. This type of architecture also provides constant monitoring without any active participation by Subject 107 being monitored. Bio-Information Unit 100 automatically collects the information from Sensor Array 215 and transmits it to Bio-Information Modem 103 whenever possible, or whenever scheduled, depending on which mode of operation is programmed into Bio-Information Unit 100.

Data input and data management are handled by Treatment Provider/Subject Database 134. Treatment Provider/Subject Database 134 is actually a combination of databases that support all of the processes in the Bio-Information Network 104. Treatment Provider/Subject Database 134 includes input and management of the Bio-Information Network 104 data, the Treatment Provider/Subject data, and any specific information relating to Treatment Provider 105, and the subject or patient data, including their individual monitoring and communications schedules and the device information for the Bio-Information Modems 103 and Bio-Information Units 100 assigned to them. This information includes what type of sensor arrays are being monitored by Bio-Information Unit 100, along with the special programs needed for Bio-Information Modem 103 and Bio-Information Unit 100 to operate correctly with the desired sensor configuration. By storing the programs in Bio-Information Network 104, Bio-Information Unit 100 can be generic in nature until it is assigned to a Subject 107 and the specific sensors that are to be monitored are assigned. After assigning the sensors, Bio-Information Network 104 will then select the appropriate software program required for monitoring the sensors and use it to remotely re-program Bio-Information Unit 100, there by specializing the unit for use with the appropriate sensors.

Treatment Provider/Subject Database 134 stores all of the readings, errors, and other information that is received from all Bio-Information Modems 103 and Bio-Information Units 100 as well as any device information that needs to be stored and monitored. Treatment Provider/Subject Database 134 provides a complete historical record of all readings and alerts for all Subjects 107 being monitored in the bio-information system.

The Situation Analyzer 124 is used to parse the data and apply a known set of rules and instructions for handling the raw data and parsing it into a limited number of categories. This includes applying any special instructions specific to the types of sensors being monitored. These categories can be broken down as follows:

Reading Data: Includes all information that has been read by the sensor arrays.

Equipment Alert: Includes Power up alarms received from the Bio-Information Unit 100, equipment failure alerts and any type of sensor malfunction information or equipment failure that is received.

Communication Alerts: Includes No Modem Communication, No Bio-Information Unit Communication, Modem missed scheduled call-in time alerts, and Bio-Information Unit missed scheduled call-in time alerts.

Equipment Maintenance: Includes alerts for scheduled maintenance, non-scheduled maintenance, and software downloads.

Equipment Assignment: Includes alerts for equipment now assigned to a subject and equipment removed from a subject.

Situation Analyzer 124 will make inquires to Workflow Instructions 128 to get direction on what is the default or specific action that should be applied to the message that was just received. Situation Analyzer 124 will then use those instructions and any historical data relating to similar messages to make a decision as to what to do with the message just received. Situation Analyzer 124 can also monitor historical data and escalate the severity of alert messages if there is a pattern emerging in the data that would require more immediate attention. Situation Analyzer 124 can also monitor historical data to detect trends in the data and then provide feedback to Subject 107 automatically by sending messages to Bio-information Modem 103 to display the feedback information on LCD Display 320. Once Situation Analyzer 124 has made its decision, it will pass the message to Alert Manager 130. Alert Manager 130 will inquire to Workflow Instructions 128 for direction on what should be done with this message. Alert Manager 130 will then present the alert information to the monitoring personnel upon request and prompt them for some type of action required to address the alert. The main categories of alert management can be broken down as:

Review/Report the information.

Take Action: by monitoring personnel or some other person in a monitoring role.

Snooze the alert.

Log all action that is required for the alert.

Change the Status of the Alert: by taking the appropriate action the alert can now be resolved. Once resolved, the database will reflect this status and remove the Alert from the new information screens.

Situation Analyzer 124 will then check to see if the message that is being dealt with requires any type of immediate notification of a treatment provider. If it does, then Situation Analyzer 124 will send the message to Notification Server 132. Notification Server 132 will then inquire to Supervising Agency/Subject Database 134 to see what method of notification is preferred by the monitoring person, and then execute the notification method, such as sending an e-mail sending a fax, sending a phone mail message, or sending a page to the appropriate person.

Thus, the method and system of the present invention offers multiple levels of alert ranging from alerts generated by Bio-Information Unit 100, from Bio-Information Modem 103, and from Bio-Information Network 104. The flexible and changeable scheduling at the Subject 107 level allows for more timely intervention for all of the Subjects 107 being monitored who are having problems.

Having described the present invention, it will be understood by those skilled in the art that many changes in construction and circuitry and widely differing embodiments and applications of the invention will suggest themselves without departing from the scope of the present invention.

What is claimed is:

1. A system for continuous passive monitoring of bio-information of a human subject comprising:
    a bio-information unit adapted to be attached to the human subject, wherein said bio-information unit takes a plurality of bio-sensor readings at predetermined time intervals according to a first schedule stored in a first memory in said bio-information unit without active participation by the human subject, wherein said plurality of bio-sensor readings are stored in said first memory;
    a bio-information modem in communication with said bio-information unit, wherein said plurality of bio-sensor readings stored in said first memory are communicated from said bio-information unit to said bio-information modem at predetermined time intervals according to said first schedule through radio frequency signals without active participation by the human subject, wherein said plurality of bio-sensor readings are stored in a second memory in said bio-information modem;
    a bio-information network in communication with said bio-information modem, wherein said plurality of bio-sensor readings stored in said second memory are communicated from said bio-information modem to said bio-information network at predetermined time intervals according to a second schedule stored in said second memory through a first communication link without active participation by the human subject, and further wherein said bio-information network analyzes said plurality of bio-sensor readings to determine if an alert condition exists; and
    a treatment provider facility in communication with said bio-information network, wherein said bio-information network communicates an alert to said treatment provider facility through a second communication link when said alert condition exists.

2. The system according to claim 1 further comprising:
    a plurality of bio-information units each of which are adapted to be attached to a one of a plurality of human subjects, wherein each of said plurality of bio-information units takes a plurality of bio-sensor readings at predetermined time intervals according to a plurality of first schedules stored in a plurality of first memories in said plurality of bio-information units without active participation by said plurality of human subjects, wherein said plurality of bio-sensor readings are stored in said plurality of first memories;
    a plurality of bio-information modems, wherein each of said plurality of bio-information modems is paired with and in communication with a one of said plurality of bio-information units adapted to be attached to said one of a plurality of human subjects, wherein said plurality of bio-sensor readings stored in said plurality of first memories are communicated from each of said plurality of bio-information units to its paired said plurality of bio-information modems at predetermined time intervals according to said plurality of first schedules through a plurality of radio frequency signals without active participation by said plurality of human subjects, wherein said plurality of bio-sensor readings are stored in a plurality of second memories in said plurality of bio-information modems, and further wherein each of said plurality of bio-information modems is in communication with said bio-information network wherein said plurality of bio-sensor readings stored in said plurality of second memories are communicated from said plurality of bio-information modems to said bio-information network at predetermined time intervals according to a plurality of second schedules stored in said plurality of second memories through a plurality of first communication links; and
    a plurality of treatment provider facilities in communication with said bio-information network, wherein each of said plurality of human subjects are associated with a one of said plurality of treatment provider facilities, and each of said plurality of treatment provider facilities can access through an internet connection to said bio-information network said plurality of bio-sensor readings for each of said plurality of human subjects associated with said one of said plurality of treatment provider facilities.

3. The system according to claim 2 wherein said bio-information network communicates automatically or on a periodic basis to said plurality of treatment provider facilities said plurality of bio-sensor readings communicated from each of said plurality of bio-information modems paired to said plurality of bio-information units for each of said plurality of human subjects associated with a one of said plurality of treatment provider facilities.

4. The system according to claim 1 wherein said bio-information unit communicates to said bio-information modem through said radio frequency signals any errors and diagnostic data.

5. The system according to claim 4 wherein said bio-information modem, upon receiving at least a one of said plurality of bio-sensor readings, said errors, and said diagnostic data, or upon a predetermined time interval occurring, will establish said first communication link with said bio-information network and communicate said at least a one of said plurality of bio-sensor readings, said errors, and said diagnostic data to said bio-information network.

6. The system according to claim 5 wherein said bio-information network, upon said first communication link being established with said bio-information modem, executes a series of inquiries to validate said bio-information modem.

7. The system according to claim 4 wherein said bio-information network further comprises:
    a web-hosted database server for storing said plurality of bio-sensor readings, said errors, and said diagnostic data.

8. The system according to claim 7 wherein said treatment provider facility accesses said web-hosted database server through an internet connection and a secure dedicated web site.

9. The system according to claim 4 wherein said bio-information network analyzes said plurality of bio-sensor readings, said errors, and said diagnostic data into a plurality of categories, and if any immediate notification action needs to be taken, said bio-information network performs a notification operation to a monitoring personnel associated with said treatment provider facility.

10. The system according to claim 9 wherein said notification operation is a one of an e-mail message, a facsimile transmission, a page to a pager, a text message, a call to a telephone, and a call to a cellular telephone.

11. The system according to claim 9 wherein said treatment provider facility, through said web-hosted database server through said internet connection, customizes a frequency of taking said plurality of bio-sensor readings and customizes a method of notification for said notification operation.

12. The system according to claim 1 wherein each of said plurality of bio-sensor readings are time and date stamped by said bio-information unit.

13. The system according to claim 1 wherein said bio-information modem can transmit to said bio-information unit through radio frequency signals said first schedule comprising a reading schedule and a communication schedule, and at least a one of a sensor configuration data and an other operational information.

14. The system according to claim 1 wherein when said communication of said plurality of bio-sensor readings from said bio-information unit to said bio-information modem fails at said predetermined time intervals, said bio-information unit repeats said communication attempt after waiting a specified time period until confirmation of transfer of said plurality of bio-sensor readings is received from said bio-information modem.

15. The system according to claim 1 wherein when said communication of said plurality of bio-sensor readings from said bio-information modem to said bio-information network fails at said predetermined time intervals, said bio-information modem repeats said communication attempt after waiting a specified time period until confirmation of transfer of said plurality of bio-sensor readings is received from said bio-information network.

16. The system according to claim 1 wherein the continuous passive monitoring of bio-information of a human subject may be done twenty-four hours a day, seven days a week, 365 days a year.

17. The system according to claim 1 wherein said plurality bio-sensor readings are at least a one of a blood oxygen reading, blood carbon dioxide reading, insulin level reading, heart rate reading, temperature reading, respiration reading, and any other biological data reading based on a specific bio-sensor in the bio-information unit.

18. A method for continuous passive monitoring of bio-information of a human subject comprising the steps of:
(a) attaching a bio-information unit to the human subject;
(b) taking a plurality of bio-sensor readings by said bio-information unit at predetermined time intervals according to a first schedule stored in a first memory in said bio-information unit without active participation by the human subject;
(c) storing said plurality of bio-sensor readings in said first memory;
(d) communicating said plurality of bio-sensor readings stored in said first memory from said bio-information unit to a bio-information modem at predetermined time intervals according to said first schedule through radio frequency signals without active participation by the human subject;
(e) storing said plurality of bio-sensor readings in a second memory in said bio-information modem;
(f) communicating said plurality of bio-sensor readings stored in said second memory from said bio-information modem to a bio-information network at predetermined time intervals according to a second schedule stored in said second memory through a first communication link without active participation by the human subject;
(g) analyzing said plurality of bio-sensor readings by said bio-information network to determine if an alert condition exists; and
(h) communicating an alert to a treatment provider facility through a second communication link when said alert condition exists.

19. The method according to claim 18 further comprising the steps of:
attaching each of a plurality of bio-information units to a one of a plurality of human subjects;
taking a plurality of bio-sensor readings by said plurality of bio-information units at predetermined time intervals according to a plurality of first schedules stored in a plurality of first memories in said plurality of bio-information units without active participation by said plurality of human subjects;
storing said plurality of bio-sensor readings in said plurality of first memories;
communicating said plurality of bio-sensor readings stored in said plurality of first memories from said plurality of bio-information units to a plurality of bio-information modems at predetermined time intervals according to said plurality of first schedules through a plurality of radio frequency signals, wherein each of said plurality of bio-information modems is paired with and in communication with a one of said plurality of bio-information units attached to said one of a plurality of human subjects;
storing said plurality of bio-sensor readings in a plurality of second memories in said plurality of bio-information modems;
communicating said plurality of bio-sensor readings stored in said plurality of second memories from said plurality of bio-information modems to said bio-information network at predetermined time intervals through a plurality of first communication links;
analyzing said plurality of bio-sensor readings from said plurality of bio-information modems by said bio-information network to determine if any alert conditions exist; and
communicating a plurality of alerts to a plurality of treatment provider facilities through a plurality of second communication links when said alert conditions exist, wherein each of said plurality of human subjects are associated with a one of said plurality of treatment provider facilities, and each of said plurality of treatment provider facilities can access through an internet connection to said bio-information network said plurality of bio-sensor readings for each of said plurality of human subjects associated with said one of said treatment provider facilities.

20. The method according to claim 19 further comprising the step of:
communicating by said bio-information network automatically or on a periodic basis to said plurality of treatment provider facilities said plurality of bio-sensor readings communicated from each of said plurality of bio-information modems paired to said plurality of bio-information units for each of said plurality of human subjects associated with a one of said plurality of treatment provider facilities.

21. The method according to claim 18 further comprising the step of:
  communicating by said bio-information unit to said bio-information modem through said radio frequency signals any errors and diagnostic data.

22. The method according to claim 21 further comprising the steps of:
  establishing said first communication link with said bio-information network upon receiving at least a one of said plurality of bio-sensor readings, said errors, and said diagnostic data, or upon a predetermined time interval occurring;
  validating by said bio-information network said bio-information modem by executing a series of inquiries to said bio-information modem; and
  upon successful validation, communicating said at least a one of said plurality of bio-sensor readings, said errors, and said diagnostic data to said bio-information network through said first communication link.

23. The method according to claim 22 further comprising the step of:
  storing said plurality of bio-sensor readings, said errors, and said diagnostic data in a web-hosted database server in said bio-information network.

24. The method according to claim 23 further comprising the step of:
  accessing said web-hosted database server by said treatment provider facility through an internet connection and a secure dedicated web site.

25. The method according to claim 24 further comprising the steps of:
  analyzing by said bio-information network said plurality of bio-sensor readings, said errors, and said diagnostic data into a plurality of categories; and
  applying a set of rules to said plurality of categories; and
  communicating an automatic alert to a monitoring personnel associated with said treatment provider facility when a rule is satisfied.

26. The method according to claim 25 wherein said automatic alert is a one of an e-mail message, a facsimile transmission, a page to a pager, a text message, a call to a telephone, and a call to a cellular telephone.

27. The method according to claim 25 further comprising the step of:
  customizing, by said treatment provider facility through said web-hosted database server through said internet connection, a frequency of taking said plurality of bio-sensor readings and a method of notification for said automatic alert.

28. The method according to claim 18 further comprising the step of:
  time and date stamping by said bio-information unit each of said plurality of bio-sensor readings.

29. The method according to claim 18 further comprising the step of:
  transmitting by said bio-information modem through radio frequency signals to said bio-information unit said first schedule comprising a reading schedule and a communication schedule, and at least a one of a sensor configuration data and an other operational information.

30. The method according to claim 18 further comprising the step of:
  when said communication of said plurality of bio-sensor readings from said bio-information unit to said bio-information modem fails at said predetermined time intervals, repeating by said bio-information unit said communication attempt after waiting a specified time period until confirmation of transfer of said plurality of bio-sensor readings is received from said bio-information modem.

31. The method according to claim 18 further comprising the step of:
  when said communication of said plurality of bio-sensor readings from said bio-information modem to said bio-information network fails at said predetermined time intervals, repeating by said bio-information modem said communication attempt after waiting a specified time period until confirmation of transfer of said plurality of bio-sensor readings is received from said bio-information network.

32. The method according to claim 18 wherein steps (b) through (h) may be performed twenty-four hours a day, seven days a week, 365 days a year.

33. A bio-information system for continuous passive remote monitoring of a human subject comprising:
  a bio-information unit having a processing means and a first memory;
  a configurable sensor array connectable to and controlled by said processing means for taking a plurality of bio-sensor readings of the human subject at predetermined time intervals according to a first schedule stored in said first memory without active participation by the human subject, wherein said plurality of bio-sensor readings are stored in said first memory;
  a radio frequency transceiver means connectable to and controlled by said processing means for transmitting said plurality of bio-sensor readings through radio frequency signals;
  a bio-information modem having a second memory in communication with the bio-information unit, wherein said bio-information unit communicates said plurality of bio-sensor readings stored in said first memory to said bio-information modem at predetermined time intervals according to said first schedule through said radio frequency signals through said radio frequency transceiver without active participation by the human subject, wherein said plurality of bio-sensor readings are stored in said second memory; and
  a communication means within said bio-information modem for transmitting said plurality of bio-sensor readings received from said bio-information unit stored in said second memory at predetermined time intervals without active participation by the human subject.

34. The bio-information system of claim 33 further comprising:
  a battery for supplying power to the bio-information unit; and
  an attachment means for attaching the bio-information unit to the human subject.

35. The bio-information system of claim 34 further comprising:
  a main program executable by said processing means for controlling the operation of the bio-information unit, wherein said main program is downloadable from said bio-information modem through said radio frequency signals to said radio frequency transceiver means through said processing means for storage in said first memory.

36. The bio-information system of claim 35 further comprising:
  a communication alert and a no bio-information unit communication alert, wherein when the bio-information unit attempts to communicate with said bio-information modem at times designated in said first schedule, and when the bio-information unit fails to communicate with said bio-information modem at a scheduled communication time, said bio-information modem generates said communication alert along with a date and time of the failed communication, and further wherein, when the bio-information unit fails to communicate with said bio-information modem for a predetermined period of time, said bio-information modem generates said no bio-information unit communication alert along with a present date and time.

37. The bio-information system of claim 36 further comprising:
a reed relay connectable to said processing means, wherein passing a magnet in proximity to said reed relay overrides said first schedule and activates the bio-information unit to take another plurality of bio-sensor readings with said configurable sensor array, and the bio-information unit attempts to communicate said another plurality of bio-sensor readings through said radio frequency transceiver through said radio frequency signals to said bio-information modem.

38. The bio-information system of claim 33 wherein the continuous remote monitoring of the human subject may be done twenty-four hours a day, seven days a week, 365 days a year.

39. The bio-information system of claim 33 wherein said configurable sensor array further comprises:
at least one sensor, wherein said at least one sensor is designed to capture at least a one of a blood oxygen reading, blood carbon dioxide reading, insulin level reading, heart rate reading, temperature reading, respiration reading, and any other biological data reading based on said at least one sensor's design.

40. A method for continuous remote bio-information monitoring of a human subject with a bio-information unit, the method comprising the steps of:
(a) taking a plurality of bio-sensor readings with a configurable sensor array of the bio-information unit at predetermined time intervals according to a first schedule stored in a first memory in said bio-information unit without active participation by the human subject;
(b) storing said plurality of bio-sensor readings in said first memory;
(c) transmitting with a radio frequency transceiver of the bio-information unit through radio frequency signals said plurality of bio-sensor readings stored in said first memory and diagnostic data without active participation by the human subject;
(d) communicating said plurality of bio-sensor readings stored in said first memory to a bio-information modem at predetermined time intervals according to said first schedule through said radio frequency signals through said radio frequency transceiver without active participation by the human subject; and
(e) storing said plurality of bio-sensor readings in a second memory in said bio-information modem;
(f) transmitting from said bio-information modem at predetermined time intervals according to a second schedule stored in said second memory said plurality of bio-sensor readings stored in said second memory without active participation by the human subject.

41. The method according to claim 40 further comprising the step of:
performing steps (a) and (b) under the control of a central processing unit within the bio-information unit.

42. The method according to claim 41 further comprising the steps of:
inserting a battery within the bio-information unit; and
attaching the bio-information unit to the human subject.

43. The method according to claim 42 further comprising the step of:
downloading a main program from said bio-information modem through said radio frequency signals to said radio frequency transceiver to said central processing unit for storage in said first memory connectable to said central processing unit, wherein said main program is executed by said central processing unit for controlling the operation of said configurable sensor array and said radio frequency transceiver.

44. The method according to claim 40 further comprising the steps of:
when the bio-information unit fails to communicate with said bio-information modem at a scheduled communication time of said first schedule, generating a communication alert by said bio-information modem along with a date and time of the failed communication; and
overriding said communication schedule by the bio-information unit and attempting to communicate with said bio-information modem after waiting a specified time period until confirmation of said attempting to communicate is received from said bio-information modem.

45. The method according to claim 40 further comprising the step of:
when the bio-information unit fails to communicate with said bio-information modem for a predetermined period of time, generating a no bio-information unit communication alert by said bio-information modem along with a present date and time.

46. The method according to claim 40 further comprising the step of:
activating said bio-information unit and overriding said communication first schedule by passing a magnet in proximity to a reed relay connectable to said central processing unit, wherein once activated, said bio-information unit takes a bio-sensor reading with said configurable sensor array, and attempts to communicate said bio-sensor reading through said radio frequency transceiver through said radio frequency signals to said bio-information modem.

47. The method according to claim 40 wherein steps (a) and (b) may be performed twenty-four hours a day, seven days a week, 365 days a year.

* * * * *